(12) United States Patent
van der Veen et al.

(10) Patent No.: US 9,393,446 B2
(45) Date of Patent: Jul. 19, 2016

(54) MOBILE X-RAY UNIT

(71) Applicant: Nucletron B.V., Veenendaal (NL)

(72) Inventors: Johannes Simon van der Veen, Dieren (NL); Bas Woudstra, Vaassen (NL); Johan Henning, Veenebdaal (NL)

(73) Assignee: Nucletron B.V., Veenendaal (NL)

( * ) Notice: Subject to any disclaimer, the term of this patent is extended or adjusted under 35 U.S.C. 154(b) by 0 days.

(21) Appl. No.: 14/635,804

(22) Filed: Mar. 2, 2015

(65) Prior Publication Data

US 2015/0165237 A1      Jun. 18, 2015

Related U.S. Application Data

(63) Continuation of application No. 13/335,712, filed on Dec. 22, 2011, now Pat. No. 8,995,616.

(60) Provisional application No. 61/426,917, filed on Dec. 23, 2010.

(30) Foreign Application Priority Data

Dec. 22, 2010   (NL) .................................. 2005901

(51) Int. Cl.
 *A61N 5/10*   (2006.01)
 *A61B 6/08*   (2006.01)
 (Continued)

(52) U.S. Cl.
 CPC ............ *A61N 5/1071* (2013.01); *A61N 5/1049* (2013.01); *A61N 5/1075* (2013.01);
 (Continued)

(58) Field of Classification Search
 CPC .......... A61N 5/00; A61N 5/10; A61N 5/103; A61N 5/1042; A61N 5/1048; A61N 5/1049; A61N 5/1071; A61N 5/1075; A61N 5/1077; A61N 5/1083; A61N 2005/105; A61N 2005/1056; A61N 2005/1075; A61N 2005/1092; A61N 2005/1095; A61B 6/00; A61B 6/08; A61B 6/547; A61B 6/58; A61B 6/582; H05G 1/00; H05G 1/02; H05G 1/04; H01J 35/00; H01J 35/02; H01J 35/16; H01J 35/165; H01J 35/18; H01J 35/32
 USPC ........ 378/51, 56, 64, 65, 68, 91, 95, 98, 98.3, 378/98.5, 98.8, 119, 121, 140, 162–166, 378/193, 204–206, 210; 250/370.01, 250/370.06, 370.07, 370.08, 370.09, 371, 250/393, 395, 493.1, 496.1, 503.1, 522.1, 250/526
 See application file for complete search history.

(56) References Cited

U.S. PATENT DOCUMENTS 5,031,203 A   7/1991   Trecha
6,087,666 A   7/2000   Huston et al.
(Continued)

FOREIGN PATENT DOCUMENTS

DE          19730519 A1       1/1999
WO    WO 2007/064900         6/2007
            WO
WO     WO 01/64286           9/2011

OTHER PUBLICATIONS

Search Report and Written Opinion in related Netherlands Application No. 2005901, dated May 28, 2011 (9 pages).
(Continued)

*Primary Examiner* — Anastasia Midkiff
(74) *Attorney, Agent, or Firm* — Finnegan, Henderson Farabow, Garrett & Dunner LLP (57) ABSTRACT

One embodiment of the present disclosure is directed to a mobile X-ray unit. The mobile X-ray unit may include a base for accommodating a control unit for controlling an X-ray applicator and a power supply for supplying power to the X-ray applicator. The mobile X-ray unit may further include an articulated arm associated with the base and coupled to the X-ray applicator. The X-ray applicator may have an X-ray tube configured to emit an X-ray beam through an exit window to irradiate an object. The mobile X-ray unit may further include a dosimetry system adapted for real time dosimetry.

18 Claims, 10 Drawing Sheets

(51) Int. Cl.
   *H05G 1/04*   (2006.01)
   *H01J 35/32*  (2006.01)
   *H01J 35/16*  (2006.01)
   *H01J 35/02*  (2006.01)
   *A61N 5/00*   (2006.01)
   *H01J 35/00*  (2006.01)

(52) U.S. Cl.
   CPC ............... *A61N5/1083* (2013.01); *H01J 35/02* (2013.01); *H01J 35/16* (2013.01); *H01J 35/32* (2013.01); *A61B 6/08* (2013.01); *A61N 5/1048* (2013.01); *A61N 2005/005* (2013.01); *A61N 2005/105* (2013.01); *A61N 2005/1056* (2013.01); *A61N 2005/1091* (2013.01); *H01J 35/00* (2013.01); *H05G 1/04* (2013.01)

(56) References Cited

U.S. PATENT DOCUMENTS

| | | | |
|---|---|---|---|
| 6,108,399 A | 8/2000 | Hernandez-Guerra et al. | |
| 6,241,670 B1 | 6/2001 | Nambu | |
| 6,267,502 B1 | 7/2001 | McNeirney et al. | |
| 6,302,581 B1 | 10/2001 | Sliski et al. | |
| 6,702,459 B2 | 3/2004 | Barnes et al. | |
| 7,108,423 B2 | 9/2006 | Schmitt | |
| 8,929,511 B2 * | 1/2015 | van der Veen et al. | 378/65 |
| 8,995,616 B2 * | 3/2015 | van der Veen et al. | 378/65 |
| 2004/0184579 A1 | 9/2004 | Mihara et al. | |
| 2006/0173233 A1 | 8/2006 | Lovoi | |
| 2007/0076847 A1 | 4/2007 | Pellegrino et al. | |
| 2007/0076851 A1 | 4/2007 | Pellegrino | |
| 2009/0190722 A1 | 7/2009 | Windt | |
| 2010/0246766 A1 | 9/2010 | Kindlein et al. | |
| 2010/0280374 A1 | 11/2010 | Roberts et al. | |

OTHER PUBLICATIONS

TOPEX, Inc., "SRT 100 Superficial Radiotherapy System for the Treatment of Skin Cancer," http://www.harpell.ca/wp-content/uploads/2009/11/topexbrochure_c10.pdf, (6 pages).

TOPEX, Inc., "Regulatory Information", http://www.tpcexmedical.com/product2.html, 2007 (1 page).

* cited by examiner

MOBILE X-RAY UNIT

CROSS-REFERENCE TO RELATED APPLICATIONS

This is a continuation of Application No. 13/335,712, filed Dec. 22, 2011, which claims the benefit of priority based on U.S. Provisional Patent Application No. 61/426,917, filed Dec. 23, 2010, and Netherlands Patent Application No, 2005901, filed Dec. 22, 2010, which are all incorporated herein by reference.

FIELD OF THE INVENTION

The present disclosure relates generally to a mobile X-ray unit. The present disclosure further relates to a method for dosimetry control using an X-ray beam emitted from the mobile X-ray unit.

BACKGROUND OF THE INVENTION

The incidence rate of skin cancer has substantially increased in the last decade of the $20^{th}$ century. It is appreciated that over 1.3 million new skin cancers are diagnosed annually, which is increasing at a rate of about 5% per year. Increased exposure to the sun without skin protection and a decreased ozone layer are regarded as the main causes of this increase—a problem estimated to be costing over 1 billion Euros in annual medical treatment expenses. Over 80% of skin cancers occur in the head and neck regions with 50% occurring in patients over 60 years of age. It is expected that a portion of the senior population will double in year 2025 compared to the present demographics. Because of the growing incidence of skin cancer and increasing share of the senior population in the overall demographics, much focus has been placed on cancer treatments and cancer treatment logistics.

Non-proliferative cancers, which are defined by substantially superficial lesions, may be treated in different ways. In one example, non-proliferative cancers may be treated surgically. Surgery, may, however, have certain drawbacks, such as, for example, long waiting lists, complications related to post-treatment care, and risk of infection. Alternatively, patients may undergo irradiation using electrons of soft X-rays. Irradiation may have an advantage of being non-invasive and of a short duration (a treatment session may be as short as 2 to 4 minutes). It will be appreciated that usually the integral treatments using radiotherapeutic techniques may require a number of sessions.

Recently, the use of a mobile and portable X-ray unit has been suggested, which may be used inside a hospital radiotherapy department. An embodiment of such portable unit is described in US 2007/0076851. Existing X-ray units include an X-ray source and a filtering device having a plurality of filters rotatably arranged with respect to a focal point of the X-ray tube for changing filtering characteristics on demand. The plurality of filters are arranged in a filtering device, which is transversely arranged with respect to a longitudinal axis of the X-ray tube. In existing devices, the X-ray applicator is positioned at some distance from the patient's skin. Existing devices have certain drawbacks. In one example, there may be poor control resulting in difficulty delineating between the X-ray beam emitted from the X-ray applicator and a treated region on the patient.

SUMMARY OF THE INVENTION

It is an object of the disclosure to provide an improved mobile X-ray unit. In particular, it is an object of the disclosure to provide a mobile X-ray unit having an X-ray beam delivered in a controlled fashion. To this end, the mobile X-ray unit, according to the present disclosure, may include a built-in dosimetry system adapted to carry out on-line or real-time dosimetry.

It will be appreciated that the terms 'mobile' and 'portable' in the context of the present application may be interchanged as these terms equally relate to an easily moved or transported device, for example, a device which may be moved or transported by a single individual.

The dosimetry system may be built into the X-ray tube or the X-ray applicator. Additionally and/or alternatively, the dosimetry system may be configured between an exit window of the X-ray applicator and a target region of an object (i.e., a patient) while being connected to a control unit of the mobile X-ray unit.

It may be advantageous to provide a dosimetry system which may be configured to deliver information substantially in real time, on the radiation dose distribution at or near the target region. The dosimetry system may include a film, a thermoluminescent device, or a semiconductor detector. However, it will be appreciated that other types of commonly known dosimeters may be used as well. For example, a suitable ionization chamber may be used, having a parallel plate configuration, like a Markus chamber. These devices may be useful for controlling a profile of the X-ray beam.

When the dosimetry system is positioned inside the X-ray applicator or inside the X-ray tube, the dosimetry system may be positioned so as to be outside a portion of the X-ray beam used for irradiating the patient. It will be appreciated that because the X-rays are generated substantially in three-dimensions, such placing of the dosimetry system is feasible.

In one embodiment, the dosimetry system may be calibrated based on the absolute dose delivered by the X-ray tube. In this way, reliable real-time dosimetry may be carried out.

It will be appreciated that it may be possible to either use a constant calibration value for converting the detector read-out signal into a delivered dose, or, alternatively, to use a suitable equation, correcting for the lifetime of the detector, and/or for time to warm-up of the X-ray tube. In some embodiments, it may be possible to use a calibration factor which may be dependent on the position and/or angle of the X-ray applicator. This may be beneficial, as changes in the alignment of internal components of the X-ray applicator may cause a deviation of the delivered dose.

In some embodiments, the dosimetry system may be configured to transmit a control signal to a control unit of the mobile X-ray unit after the X-ray tube has been switched on. In addition, the dosimeter system may be configured to transmit a signal to the control unit of the mobile X-ray unit when a prescribed dose has been delivered.

In some embodiments, the dosimetry system may include a dose meter. The dose meter may be positioned between the X-ray applicator and a target region of an object (i.e., patient). This arrangement may be advantageous, as the dose meter may, by virtue of its material, establish an electronic equilibrium at or near the surface of the object. As a result, the percentage depth dose build-up inside the object may be determined relative to an absolute value of the surface dose. It will be appreciated that for skin treatment the surface dose may not be higher than 137% of the prescribed depth dose. Usually the prescribed depth dose is specified at a depth of 5 mm from the skin surface.

Due to a presence of an additional material (a film or a detector) the percentage depth dose inside the object may be changed to reduce the surface dose when normalized with the dose at 5 mm depth.

In various embodiments, the dosimetry system may include a digital readout device. It may be advantageous to enable real-time data acquisition and data processing by using a digital dosimeter, which may be connected to the control unit of the mobile X-ray unit so as to facilitate a substantially direct hardware response should the measured dose substantially deviate from the prescribed dose. It will be appreciated, that a film may be used for dosimetry purposes which may be subsequently read-out using a digital densitometer.

It will be appreciated that the dosimetry system may be arranged to electronically communicate with the control unit. In particular, the dosimetry system may have either an analogue or a digital signal as an output. Those skilled in the art will readily appreciate which electronic devices (if any) may be necessary for enabling data communication between the dosimetry system and the control unit of the mobile X-ray unit.

In various embodiments, the dosimetry system may be configured enable verification of at least a position and geometry of a generated X-ray field.

The dosimetry system, i.e. a film or a device (thermoluminiscent, ionization chamber or a semiconductor), may include a plurality of measuring points, preferably distributed in a plane. When the dosimetry system is positioned in the X-ray field, the readings may be processed for establishing dose data across the applied field. For example, a reading at the central axis may be obtained, and a number of peripheral readings, preferably at different radial distances, may be obtained. As a result, information may be obtained regarding not only the absolute dose in the central field, but also information about beam flatness across the field. In some embodiments, the dosimetry unit may be calibrated to calculate an absolute dosimetry of an X-ray dose. Such calibration may be carried out by, for example, using a trial measurement for a known X-ray dose.

In various embodiments, the X-ray applicator may include an Indicator for visualizing at least a portion of the X-ray beam emitting from the exit surface of the applicator.

Treatment efficacy may be substantially improved when an indicator is provided for delineating at least a portion of the generated X-ray beam, like a central axis thereof, and/or a partial or a full beam geometry. In particular, an indicator may be advantageous for positioning the dosimetry system with respect to the X-ray beam. In an exemplary embodiment, the indicator is a light source. The light source may be arranged in the X-ray applicator or, alternatively, the light source may be arranged around an outer surface of the X-ray applicator. When the light source is arranged in the X-ray applicator, the light source may be configured to delineate the central axis of the X-ray beam and/or the full beam geometry. When the light source is arranged around the outer surface of the X-ray applicator, the light source may be arranged to delineate a central axis of the X-ray beam, preferably at a pre-determined distance from the X-ray applicator. This may be advantageous when the X-ray applicator is used at a standard distance from the patient's skin. However, it will be appreciated that the light source arranged around the X-ray applicator may be adjusted so as to indicate the central axis of the X-ray beam at a variety of axial distances from the X-ray applicator.

In various embodiments, the indicator includes an array of light sources concentrically arranged around the X-ray applicator. Although it may be sufficient to provide a single light source that generates a narrow beam for indicating the central axis of the X-ray beam, it may be advantageous to provide a plurality of light sources each of which generates a narrow light beam. These light beams may intersect at a given distance from the lower surface of the X-ray applicator. In this manner, the X-ray applicator may be positioned at a prescribed distance from the skin. Additionally, the dosimetry system may be positioned with respect to the X-ray beam. In order to ensure a correct coverage of the target region by the X-ray beam, the X-ray applicator may be positioned so that the indicated center of the X-ray beam is positioned substantially at a center of the target region. It will be appreciated that these embodiments function particularly well for regular shaped X-ray beams, for example, when a circular, a square, an elliptic, or a triangular collimator is used for shaping the X-ray beam.

In various embodiments, the light source may be disposed inside the X-ray applicator for generating a light beam configured to be intercepted by a collimator for providing a light image of the X-ray field emitted from the exit window.

This embodiment may be advantageous when the full shape of the X-ray beam is to be delineated such as; for example, in situations when an irregular beam shape is used. In such cases, the light source may be provided near the target region or, via a mirror, off-axis, for generating a light beam configured to be intercepted by the collimator. It will be appreciated that a direction of propagation of the light beam must essentially conform to a direction of propagation of the X-ray beam. In one embodiment, when a mirror is used, the light source may advantageously be positioned off-axis minimizing its radiation damage.

In various embodiments, the indicator includes a light source and an optical fiber configured to deliver light from the light source for interception by the collimator.

This may be advantageous as the light source may be positioned outside the X-ray applicator in order maintain the overall size of the X-ray applicator. For example, the light source may be arranged in the base of the X-ray unit and the optical fibers may run from the base to inside the X-ray applicator for suitably illuminating the collimator for obtaining a light image equivalent to that of the generated X-ray beam.

In various embodiments of the present disclosure, the Indicator may include a plurality of optical fibers distributed in the X-ray applicator in an area above the collimator for illuminating a collimator opening for causing the collimator opening to intercept the resulting light field. This embodiment may be advantageous for obtaining a light field having substantial intensity.

In various embodiments, the indicator may include a light source emitting a narrow light beam arranged Inside the applicator for delineating a longitudinal axis of the X-ray beam. Preferably, a miniature laser source may be used.

In a still further embodiment of the X-ray unit according to the invention a radiation detector may be provided inside the outer housing for detecting the X-ray beam.

It may be advantageous to provide an independent mechanism for detecting the presence of an X-ray beam. In some embodiments, the X-ray unit includes a primary timer which may set a time for the high voltage supply to deliver a predetermined radiation dose. The radiation sensor disposed inside the outer housing of the X-ray applicator may be part of a secondary timer circuit adapted to shut down the high voltage supply when the predetermined radiation dose has been delivered. In this way radiation safety control may be improved.

In some embodiments, in which a dosimetry system may provide data in real-time, the signal from the dosimetry system may be used in addition to the signal from the built in radiation detector. In particular, when the dosimetry system is arranged to verify the beam characteristic, a substantial deviation from the prescribed beam flatness may be used as a control signal to shut-down the mobile X-ray unit.

In some embodiments, the X-ray applicator includes an exit surface configured to be oriented towards a patient, the surface may be covered by an applicator cap.

It may be advantageous to provide an applicator cap, which may have many functions in use. In one example, the applicator cap may be used for protecting the exit surface of the X-ray applicator from intra-patient contamination. In another example, the thickness of the cap in a direction of the beam propagation may be sufficient for substantially eliminating electron contamination from the X-ray beam. In some embodiments, the applicator cap may be manufactured from PVDF (Polyvinylidene fluoride) and may have a thickness of about 0.4-0.7 mm, preferably 0.6 mm, across the window portion. The applicator cap may have a density of about 1.75-1.8, and preferably 1.78. In other embodiments, the applicator cap may have a thickness of 0.3-0.6 mm, and preferably 0.5 mm, across the window portion. In these embodiments, the applicator cap may have a density of 1.30-1.45, and preferably 1.39, and may be manufactured from PPSU (polyphenylsulfone). It is found that these materials may be particularly suitable as they are stable under influence of the X-rays and are suitable for different types of sterilization procedures, such as chemical sterilization, or sterilization under elevated temperatures. It will be appreciated that those skilled in the art will readily appreciate the relationship between the energy of the secondary electrons emanating from the X-ray tube and a required thickness of a given material, such as, for example plastic, glass, ceramics, sufficient for fully intercepting these electrons. In some embodiments, the applicator cap may be disposable.

It will be appreciated that the indicator configured to delineate the X-ray beam may be configured to have sufficient intensity to provide a field image through the applicator cap. Lasers may be particularly suited for this purpose. Alternatively, light emitting diodes may be used. In another embodiment, an arrangement of one or more light sources generating a narrow beam outside the X-ray applicator may be advantageous. In that embodiment, one or more sources may be arranged on respective support arm such that the respective narrow light beams are not intercepted by the applicator cap.

Another embodiment of the present disclosure is related to a method for dosimetry control of an X-ray beam emitted from a mobile X-ray unit. The mobile X-ray unit may include a base for accommodating a control unit and a power supply. The mobile X-ray unit may further include an articulated arm associated with the base. The articulated arm may be configured to support an X-ray applicator having an X-ray tube for generating an X-ray beam. The method may include measuring a parameter associated with the X-ray beam using a built-in dosimetry system. The method may further include measuring the parameter in real-time.

In various embodiments, an Indicator may be provided in or near the X-ray applicator for visually delineating at least a portion of the X-ray beam, which may assist in positioning the dosimetry system. In some embodiments, the indicator includes a light source arranged to generate a light field that may be intercepted by a collimator opening for providing visualization of the X-ray beam. In another embodiment, the indicator may include a light source arranged to delineate a longitudinal axis of the X-ray beam.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIG. 6, E-E presents a cross-section along line VII-E of the X-ray tube of FIG. 6, according to embodiments of the present disclosure.

FIG. 6, F-F presents a cross-section along line VII-F of the X-ray tube of FIG. 6, according to embodiments of the present disclosure.

DESCRIPTION OF THE EMBODIMENTS

Reference will now be made in detail to the present exemplary embodiments of the invention, examples of which are illustrated in the accompanying drawings. Wherever possible, the same reference numbers will be used throughout the drawings to refer to the same or like parts.

Figure 1A:
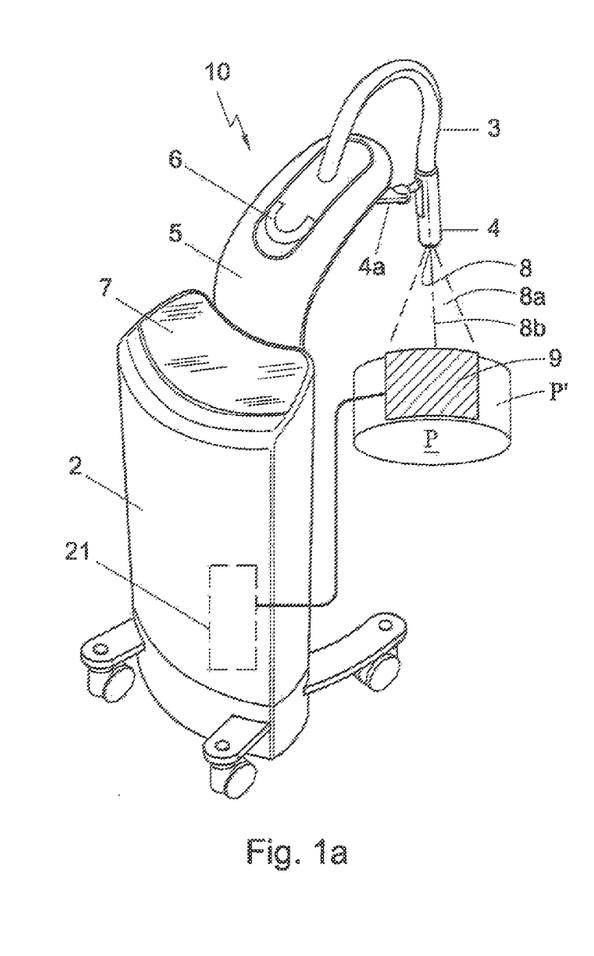
FIG. 1a presents a perspective view of a mobile X-ray unit, according to embodiments of the present disclosure.

FIG. 1a presents a partial perspective view of a mobile X-ray unit according to the present disclosure. The mobile X-ray unit 10 includes a base 2 having at least a high voltage supply unit, a cooling system, and a control unit (FIG. 2) for controlling operation of an X-ray applicator 4. The X-ray applicator 4 includes an X-ray tube (FIG. 3) disposed in an outer housing of the X-ray applicator 4. The X-ray applicator 4 may be connected to the base 2 using flexible cables 3, which may be at least partially disposed in a displaceable panel 5. The X-ray applicator 4 may be coupled to an articulated arm 4a, which may include a pivot for varying the position of the X-ray applicator 4 in space. The X-ray applicator 4 may include a longitudinal axis and an exit window 8 through which the generated X-ray beam 8a may be emitted. The articulated arm 4a may also be connected to the displaceable panel 5 to change a vertical position of the applicator 4. In some embodiments, the displaceable panel 5 may be provided with a handle 6 enabling easy manipulation thereof. The displaceable panel 5 may be guided along suitable rails for enabling a substantially smooth and shock-free displacement thereof.

In one embodiment, the X-ray applicator and the X-ray tube may be coaxially disposed. A longitudinal axis of an anode of the X-ray applicator may be substantially parallel to a longitudinal axis of the X-ray applicator so that the X-ray beam 8a may propagate from the exit window 8 having a beam axis 8b substantially corresponding to a longitudinal axis of the X-ray tube.

In various embodiments, a dosimetry system 9 may be provided to provide data on at least a portion of the X-ray field 8a at or near the surface P' of the patient P. The dosimetry system may include ionization chambers, solid state detectors, and semiconductor detectors. In one embodiment, the system may be capable of generating real-time. In some embodiments, the signal from the dosimetry system may be supplied into the control unit 21 of the mobile X-ray unit for real-time dose delivery control.

In some embodiments, an indicator may be provided to position the X-ray applicator 4 and the dosimetry system 9 with respect to a target region on the surface P' of a patient P. The Indicator may be used to delineate the X-ray field generated by the X-ray tube (FIG. 3) inside the X-ray applicator 4. In some embodiment, the indicator may be a light source, such as, for example, a light emitting diode, a laser, or the like.

The light source may be arranged either inside the X-ray applicator 4, or around the X-ray applicator 4, or it may be remotely positioned, for example in the base 2. In the latter case, light from the light from the light source (not shown) may be conducted towards the X-ray applicator using one or more optical fibers. More details on suitable light source arrangements, although not limitative, are discussed with reference to FIGS. 4a-4c.

The displaceable panel 5 may include a display 7, which may function as a suitable user interface 7a. For example, the patient data, such as a photo of the patient and/or a photo of a lesion may be provided in window 7b, whereby relevant patient information, such as the date of birth, gender, dose prescription, and dose delivery protocol may be displayed in window 7c. Buttons 7d may be provided as touch functionality for enabling entering data. Additionally and/or alternatively, suitable hardware switches or buttons may be provided as well.

In some embodiments, the display 7 may be arranged as a touch-sensitive screen for enabling suitable data input into the system. For example, the display panel may comprise buttons or switches for switching the indicator (i.e., light source) on. Optionally, the Indicator may always be on when the X-ray unit is switched on. The user interface may further be used to input a prescribed dose and, possibly, a prescribed dose distribution, especially when dose modifiers are used for providing a gradient in the dose profile across the X-ray field. The user interface may also be arranged to display data on actual dose delivery and dose distribution profile during the treatment. It will be appreciated that by using the dosimetry system the dose delivery protocol may be compared with actual dose delivery data in real time and, if necessary, the actual dose delivery may be corrected in real time and/or during further sessions should a discrepancy in prescribed and delivered dose of more than 1% occur.

Figure 1B:
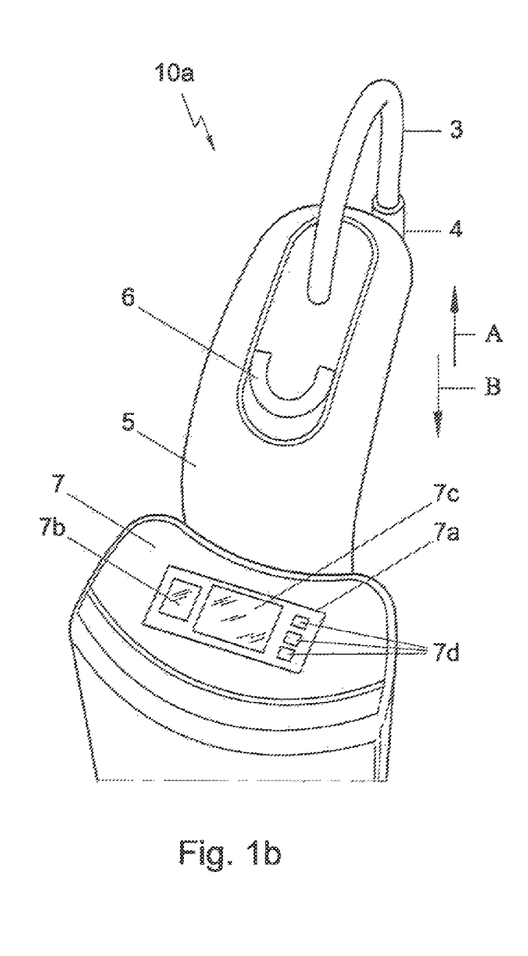
FIG. 1b presents a partial perspective view of a mobile X-ray unit illustrating movement of a displaceable panel, according to embodiments of the present disclosure.

FIG. 1b presents a partial perspective view of the mobile X-ray unit illustrating movement of the displaceable panel. In this enlarged view 10a, specific elements of the displaceable panel 5 are depicted. A handle 6 may be implemented as a mechanical item for pulling or pushing the displaceable panel 5. Alternatively, the handle 6 may be arranged as an electrical actuator for triggering motors (not shown) for displacing the displaceable panel 5. For example, when the handle 6 is pulled the motors may be activated for causing the panel 5 to displace in a direction A. Pushing of the handle 6 may cause lowering of the panel 5 in a direction B. In some embodiments, the mobile X-ray unit 10 includes stops, limits, or other known structures for limiting the movement of the displaceable panel 5. This may be advantageous for ensuring mechanical stability of the mobile X-ray unit 10 (limitation of the upper level) and may also be beneficial for preventing cable damage (limitation of the lower level). In some embodiments, the displaceable panel 5 may travel along built-in rails whose length may be chosen for limiting the displacement range of the panel 5 in a desirable way.

Figure 1C:
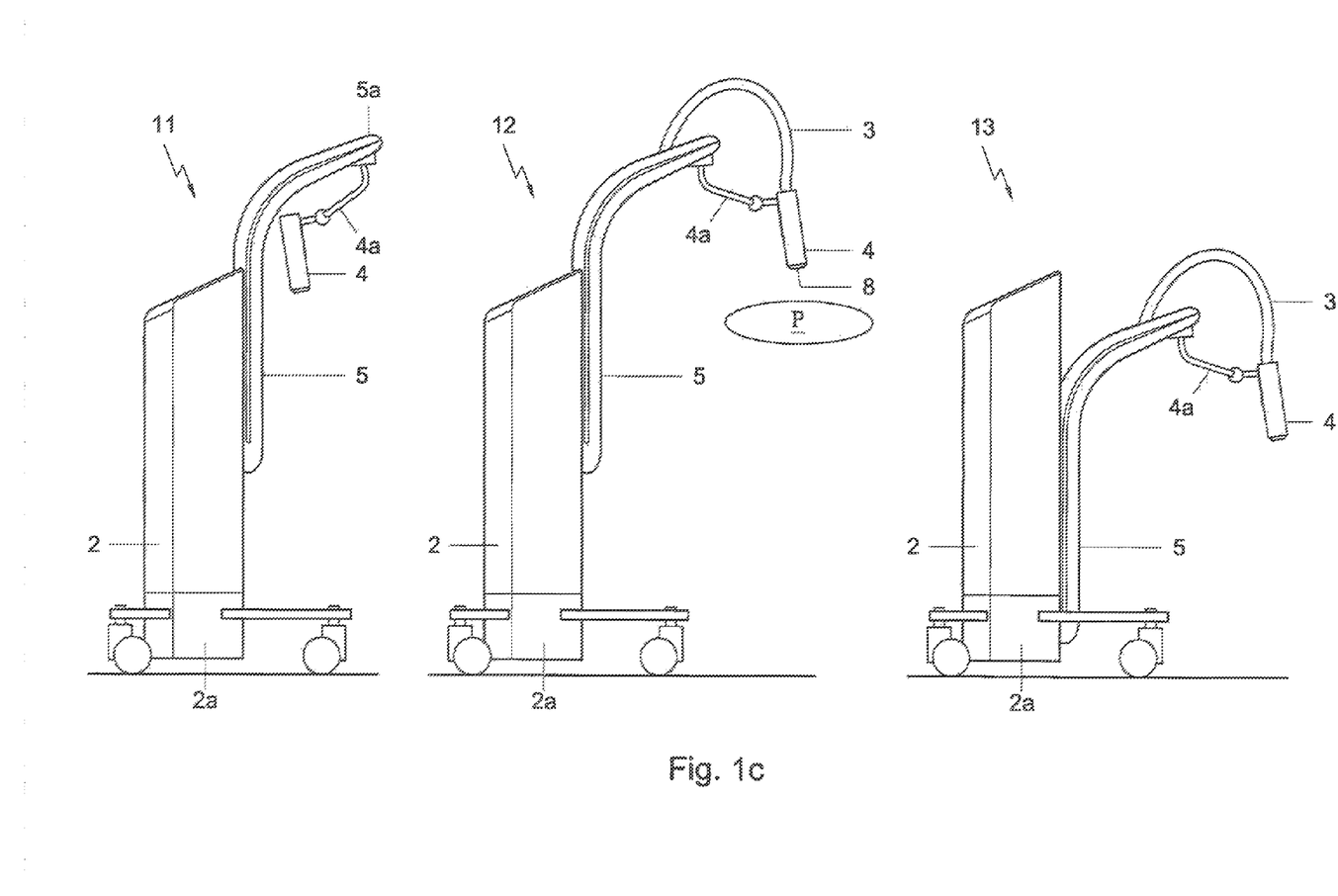
FIG. 1c presents a schematic view of the mobile X-ray unit shown in FIGS. 1a and 1b, illustrating displacement of an X-ray applicator of the X-ray unit relative to a base of the mobile X-ray unit, according to embodiments of the present disclosure.

FIG. 1c illustrates the displacement of the X-ray applicator 4 of the X-ray unit 10. It will be understood that the mobile X-ray unit 10 may be configured so as to support a broad range of translational and rotational movements of the X-ray applicator 4.

In view 11, the X-ray applicator 4 is in a retracted position. It will be appreciated that cabling is not depicted for clarity reasons. The retracted position may be suitable for transport of the mobile X-ray unit 10 towards a booth and/or for maneuvering the X-ray unit 10 around the patient. In order to retract the X-ray applicator 4 as close as possible to the base 2, the articulated arm 4a may be positioned under the outer portion 5a of the displaceable panel 5. For ensuring stability of the mobile X-ray unit 10 during maneuvering thereof, a load block 2a may be provided for lowering the point of gravity of the X-ray unit 10.

In view 12, the X-ray applicator 4 may be in an extended position (i.e., working position) having an X-ray exit surface 8 oriented towards a patient P. In order to suitably position the X-ray applicator 4 with respect to the patient P, the displaceable panel 5 may be moved to an intermediate position located between a lowest stand position and a highest stand position of the displaceable panel 5. The articulated arm 4a may be used for suitably rotating the X-ray applicator 4 about a rotation axis. In one embodiment, a rotation axis is selected to coincide with a direction include the X-ray beam is emitted from an exit window 8 for a vertically oriented X-ray applicator 4.

In view 13, the X-ray applicator 4 may be in a lowered position. For this purpose the displaceable panel 5 may be in its lowest position and the arm 4a may be used for orienting the X-ray applicator 4 in a desirable way.

Figure 2:
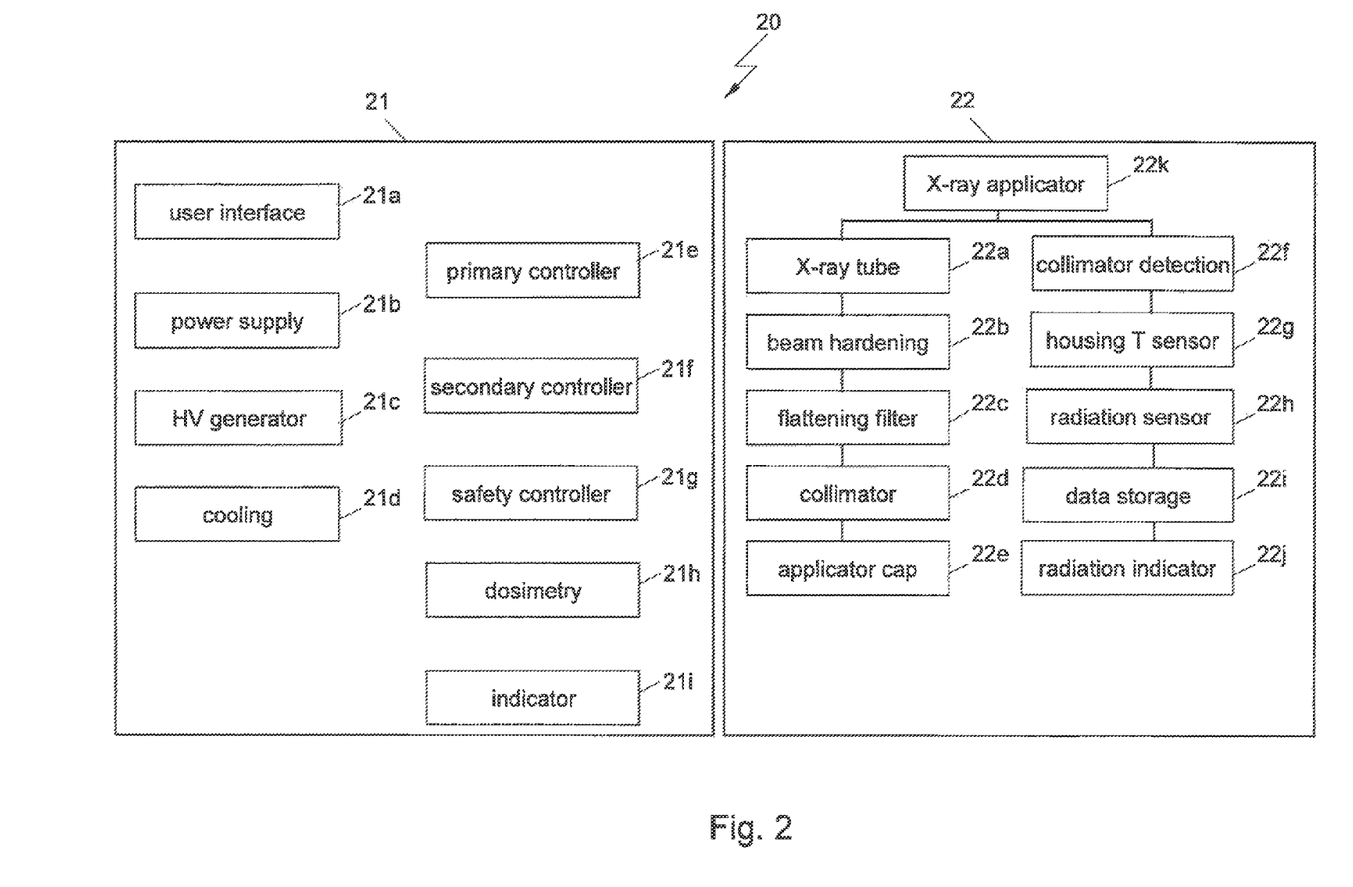
FIG. 2 presents a diagrammatic representation of the mobile X-ray unit, according to embodiments of the present disclosure.

FIG. 2 is a diagrammatic representation of the mobile X-ray unit 10 according to embodiments of the disclosure. The mobile X-ray unit 10 includes a high voltage supply, preferably adapted to generate 50-75 kV X-rays in a suitable X-ray tube, a cooling system 21d for cooling the X-ray tube during use, and a control system 21 for controlling electronic and electric parameters of sub-units of the X-ray unit during use. View 20 diagrammatically depicts main units of the control system 21 and of the X-ray applicator 22.

The control system 21 may include a hard wired user interface 21a for enabling a user to switch on and switch off of the high voltage supply 21b. In some embodiments, the high voltage supply 21b includes a high voltage generator 21c with improved ramp-up and ramp-down characteristics. The high voltage supply may be operable to deliver power of about 200 W in use. In some embodiments, the ramp-up time may be of the order of 100 ms. The hard wired Interface 21a, may also be arranged to automatically switch on the cooling system 21d when the high voltage generator 21c is switched on. In addition, the control system 21 may include a primary controller 21e arranged for controlling the dose delivery from the X-ray applicator 22.

The primary controller 21e may be provided with a primary counter adapted to register time lapsed after the X-ray radiation is initiated. The primary counter may then automatically switch off the high voltage supply 21b to the X-ray tube 22a in the event a pre-determined dose is reached. It will be appreciated that the pre-determined dose is at least dependent on the energy of the X-rays and the dose rate, which may be calibrated in advance. Where calibrated data is made available to the primary controller 21e, adequate primary dose delivery control may be achieved. In some embodiments, a secondary controller 21f may be provided for enabling an independent loop of dose delivery control. The secondary controller 21f may be connected to a dose meter accommodated inside the X-ray applicator 22 in the X-ray field before the collimator 22d. Accordingly, the dose meter may provide real-time data on actual dose delivery taking into account dose variation during ramp up and ramp down of the high voltage source. Still preferably, the control system 21 may include a safety controller 21g adapted to compare readings from the primary controller 21e and the secondary controller 21g for switching off the high voltage generator 21c after a desired dose is delivered. Additionally and/or alternatively, the safety controller 21g may be wired to guard emergency stop, door interlock, and a generator interlock.

The control system 21 may further include a dosimetry control 21h, configured to communicate with a dosimetry system on-line. It is also possible that the dosimetry control 21h may accept data from a scanned dosimetric field and update dose delivery data post-processing.

The dosimetry control 21h may be arranged to provide an interrupt signal, should the real-time dosimeter measure a substantial deviation between the prescribed dose and the measured dose. For example, the dosimetry control 21h may provide a suitable interrupt signal to the high voltage generator control 21c to switch off the high voltage generator 21c.

The control system 21 may further include an indicator controller 21i for controlling an Indicator (i.e., a light source) used to delineate at least a portion of the X-ray beam. In some embodiments, the indicator controller 21i may be linked to a power supply unit 21b for switching on the light source once the system is on. Alternatively, the light source may be switched on demand. Accordingly, the indicator controller 21i may be arranged to provide electrical power to the light source when triggered by the user. The user may provide a suitable trigger signal by a user interface, or, for example, using a dedicated hardware switch.

Figure 5:
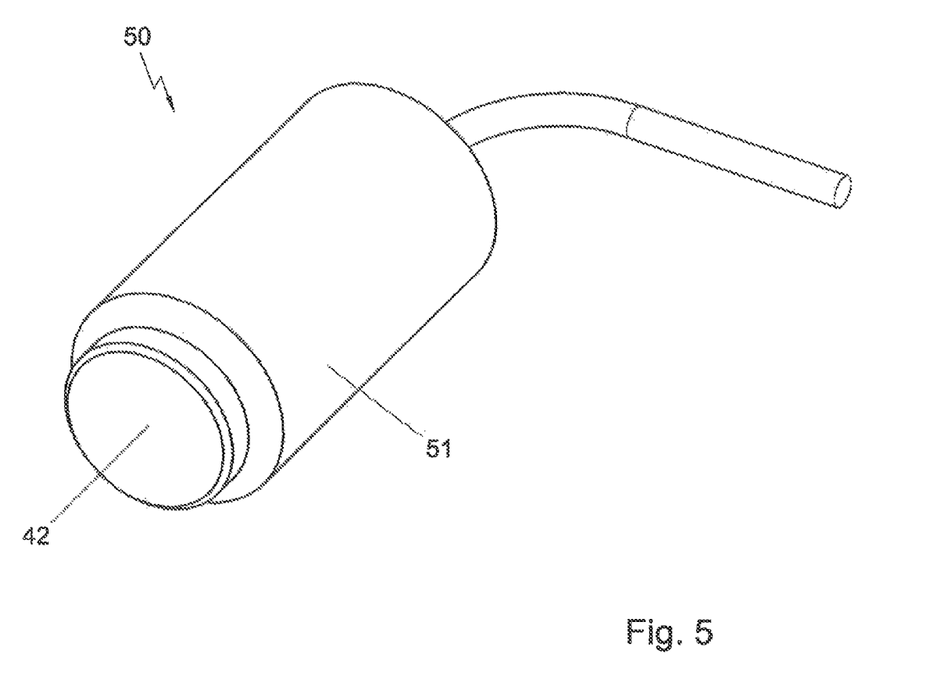
FIG. 5 presents a partial perspective view of the X-ray applicator provided with an applicator cap, according to embodiments of the present disclosure.

The X-ray applicator 22 may include an X-ray tube 22a housed in an outer housing (shielding) 22k. In the exemplary embodiment, a target, a collimator 22d, and an exit window (FIG. 1a) of the X-ray applicator 22 may be in parallel so that the generated X-ray beam may be propagated substantially parallel to a longitudinal axis of the X-ray tube 22a. The X-ray tube 22a may have a target-collimator distance of between 4 and 10 cm, and preferably 5 and 6 cm. The X-ray applicator 22 may further include a beam hardening filter 22b selected to intercept low-energy radiation and a beam flattening filter 22c, designed to intercept portions of X-ray radiation for generating a substantially flat beam profile near the exit surface of the X-ray applicator 22. Further, the X-ray applicator 22 may include one or more collimators 22d arranged to define the shape of the X-ray beam. In some embodiments, a set of collimators 22d may be used having, for example, diameters of 1, 1.5, 2, 2.5, 3, 3.5, 4, 4.5, and 5 cm. It will be appreciated that although circular collimators are discussed, collimators of any shape, such as square, elliptic or custom made collimators are possible. It may be advantageous to have an X-ray applicator 22 with automatic collimator detection device 22f configured to automatically signal which collimator is being used. In some embodiments, resistive sensing may be used to identify which collimator 22d is being used. In particular, each collimator may be provided with at least a couple of projections for bridging a resistive path provided in a collimator receptacle (FIG. 5). The resulting electrical resistance of the receptacle constitutes a signal representative of a collimator being used.

The X-ray applicator 22 may also include a built-in temperature sensor 22g adapted to monitor a temperature of the X-ray tube 22a and/or its shielding 22k. The signal from the temperature sensor 22g may be received by the control system 21 which may carry out the analysis thereof. Should the measured temperature be elevated beyond an allowable level, an alarm signal may be generated. Optionally, a shut-off signal to the high voltage generator may be provided. The X-ray applicator 22 may further include a radiation sensor 22h arranged inside the outer housing 22k for detecting X-ray radiation which may be delivered by the X-ray tube 22a. Preferably, for safety reasons the X-ray applicator 22 may include a non-volatile data storage 22i arranged for recording operational parameters of at least the X-ray tube 22a. Further, to enhance radiation safety, the X-ray applicator 22 may be provided with a radiation indicator 22j arranged for providing a visual and/or an audio output to the user and/or the patient regarding ON/OFF condition of the X-ray tube 22a. It will be appreciated that the radiation indicator 22j may include a plurality of signaling devices. In one embodiment, at least one signaling device, for example a light emitting diode (LED), may be associated with the X-ray applicator 22 and provided on the X-ray applicator 22. It is understood, however, that the signaling devices may be positioned at any other location on the mobile X-ray unit.

Figure 3:
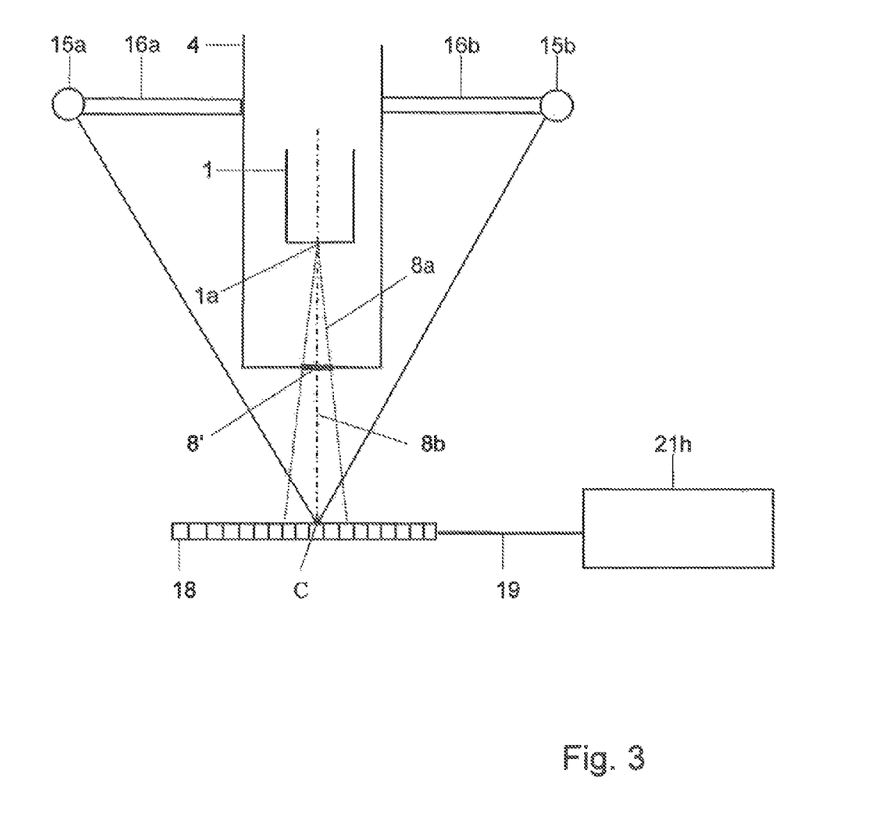
FIG. 3 presents a schematic view of a dosimetry system of the X-ray unit according to the invention.

FIG. 3 presents a schematic view of a dosimetry system of the X-ray unit. The X-ray applicator 4 discussed above may include an X-ray tube arranged with an anode 1 having a target 1a for generating a diverging X-ray beam 8a. The target 1a may be a substantially flat plate which may extend substantially perpendicular to a longitudinal axis of the anode 1. In one embodiment, the anode 1 may be aligned along axis 8b of the X-ray beam (and the X-ray tube), however, it is understood that other respective orientations are possible. The X-ray beam 8b may be emitted from an exit surface 8' of the X-ray applicator. It will be appreciated that suitable filters, a collimator, and an exit window of the X-ray tube are not depicted for clarity reasons. Accordingly, the exit surface 8' does not necessarily correspond to the exit window of the X-ray tube.

In one embodiment, an indicator such as, for example, a light source, may be used to position the X-ray applicator 4 with respect to a target region on an object (i.e., patient). In one embodiment, the indicator may include two light sources 15a, 15b configured to generate a narrow beam light. In this embodiment, the light sources 15a, 15b may be mounted on respective support arms 16a, 16b on an outer surface of the X-ray applicator 4. Preferably, the light sources 15a, 15b may be configured to provide a point in space C corresponding to the beam axis 8b. A dosimetry system may include a dosimetric device 18 that may then be centralized with respect to the point C for intercepting the X-ray beam.

In some embodiments, the mobile X-ray unit may be provided with a plurality of dosimetric devices of different size. A suitable dosimetric device 18 may be selected based on the actual beam size. In some embodiments, the dosimetric device 18 may extend further than the X-ray field for measuring an absolute dimension of the X-ray field.

In some embodiments, the dosimetric device 18 may include an array of independent measuring volumes. It will be appreciated that for this purpose a film may be used, a set of TLD devices, or an array-type semiconductor dosimeter. As a result, dose distribution across the X-ray field may be established for verification and/or for intra-fraction correction.

In some embodiments, the dosimetric device 18 may provide data in real time. In particular, the dosimetric device may be connected to a dosimetric control unit 21h, as discussed with reference to FIG. 2.

Although an embodiment of the dosimetric system is discussed with reference to the X-ray applicator provided with an indicator (i.e., light source), it will be appreciated that dosimetric system may be utilized without an Indicator to delineate the X-ray field.

Figure 4A:
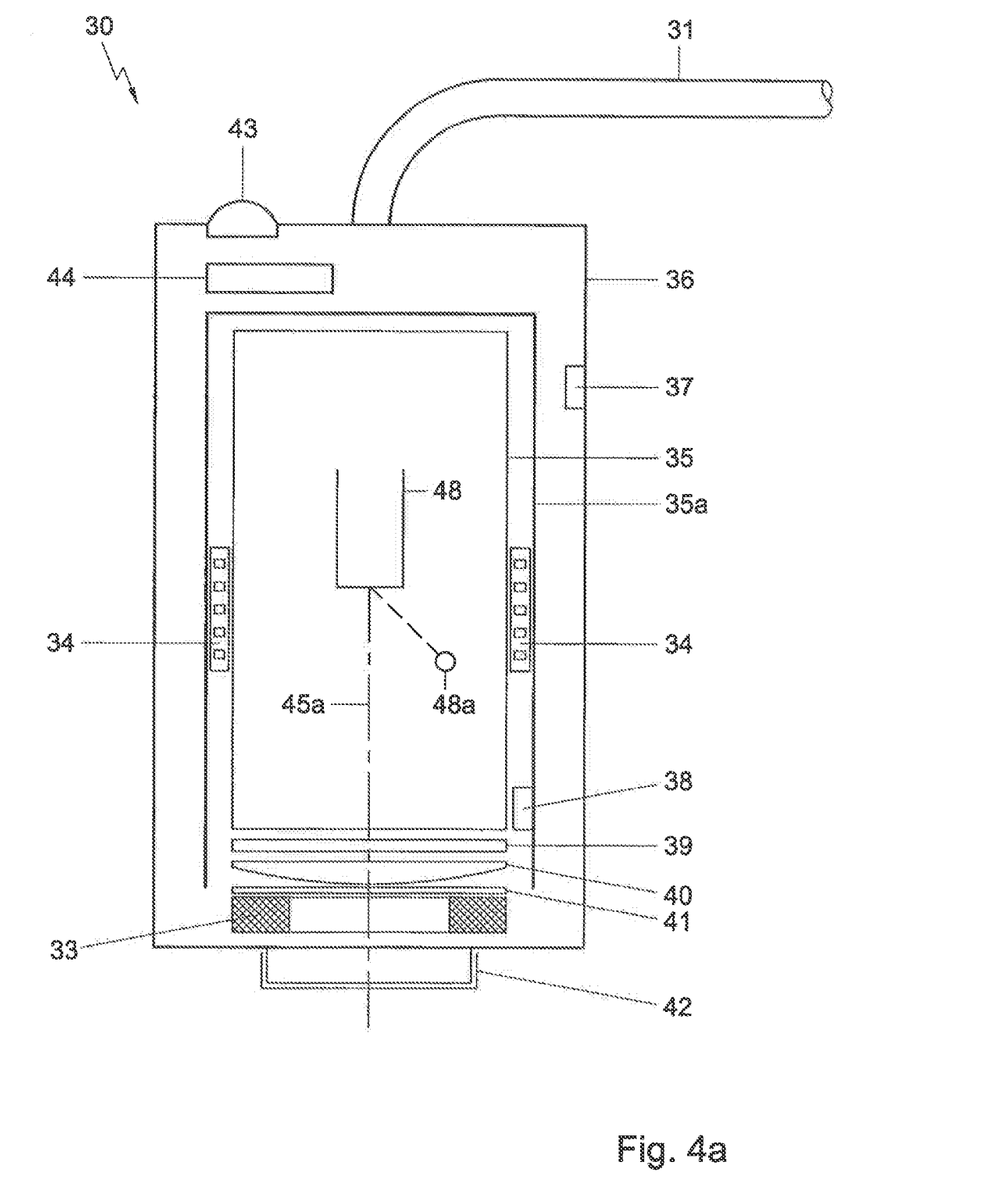
FIG. 4a presents a cross-sectional view of an X-ray applicator of the mobile X-ray unit having an indicator, according to a first embodiment of the present disclosure.

FIG. 4a presents a cross-section of an X-ray applicator of the mobile X-ray unit having an indicator, in accordance with a first embodiment of the present disclosure. The X-ray applicator 30 includes an outer housing 36 and an X-ray tube 35 disposed in the outer housing 36. The X-ray tube 35 may have an external shielding 35a, a target (not shown), and a collimator 33.

In one embodiment, the indicator may be light source 48a. The light source 48 may cooperating with a mirror 48 for emitting a light beam indicative of a two-dimensional beam of X-rays produced by the X-ray tube 35. In some embodiments, X-rays have a propagation axis 45a which coincides with a longitudinal axis of the X-ray tube 35. The light source 48a and the mirror 48 may be arranged so that the light beam may substantially propagate along the longitudinal axis of the X-ray tube 45a.

When the light beam is intercepted by a collimator 33 a visual indication and simulation of the two-dimensional X-ray beam is created. In one embodiment, the distance between a target of the anode (not shown) and the collimator 33 is in the range of 4 to 10 cm, preferably about 5 to 6 cm. Such relatively short target-collimator distance may generate an X-ray beam having a substantially narrow penumbra (1.5-1.8 mm for 20/80% lines) and good beam flatness due to a relatively small focal size.

The X-ray applicator 30 may further include a filter 39 for hardening the X-ray beam generated at the target, a beam flattening filter 40 for flattening out a beam profile, and a collimator receptacle 41 for receiving collimator 33.

A cooling system 34 may be provided so as to prevent overheating of the X-ray tube 35. In one embodiment, the cooling system 34 may be arranged in the space between the X-ray tube 35 and the shielding 35a in contact with the surface of the X-ray tube 35. A suitable coolant may be provided using a pipe 31. It is contemplated that the coolant may be water, a pressurized gas, or even a special oil. The X-ray applicator 30 may further include a temperature sensor 37.

The X-ray assembly 30 may further include a suitable radiation detector 38 connected to a radiation indicator 43. Data collected by the radiation detector 38 may be stored in a data storage unit 44.

In order to protect the X-ray exit surface (including window) of the X-ray applicator 30 from intra-patient contamination, an applicator cap 42 may be provided to cover at least the exit surface of the X-ray applicator 30. In some embodiments, the applicator cap 42 is thick enough to fully intercept secondary electrons emanating from the X-ray applicator 30. The applicator cap 42 may be manufactured from PVDF (polyvinylidene fluoride) and may be about 0.4-0.7 mm, and preferably 0.6 mm thick across the window portion. The applicator cap 42 may have density of about 1.75-1.8, and preferably 1.78. Alternatively the applicator cap 42 may be 0.3-0.6mm thick, and preferably 0.5 mm thick across the window portion. In those embodiments, the applicator cap 42 may have a density of 1.30-1.45, and preferably 1.39. Further, the applicator cap 42 may be manufactured from PPSU (polyphenylsulfone). These materials may be particularly suitable as they as stable under influence of the X-rays and are suitable for different types of sterilization procedures, such as chemical sterilization, or sterilization under elevated temperatures.

Figure 4B:
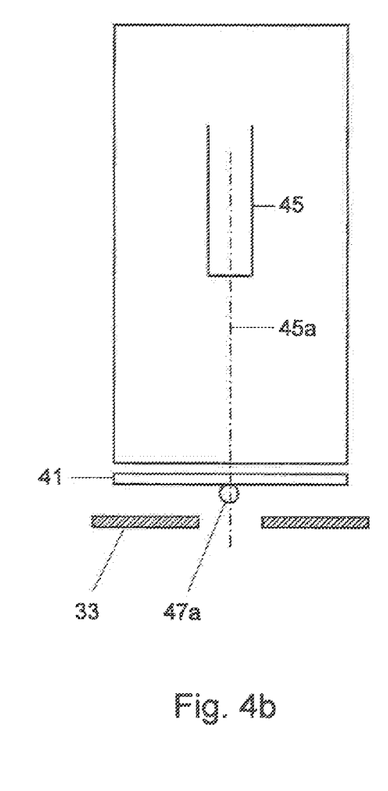
FIG. 4b presents a cross-sectional view of an X-ray applicator of the mobile X-ray unit having an indicator, according to a second embodiment of the present disclosure.

FIG. 4b presents a cross-section of an X-ray applicator of the mobile X-ray unit having an indicator, in accordance with a second embodiment of the present disclosure. In this exemplary embodiment, the indicator includes at least one optical fiber 47a connected to a light source that may be positioned remotely in, for example, base 2.

Optical fiber 47a may be provided in the collimator receptacle 41 above the collimator 33. The optical fiber 47a may be configured to generate a light field that is substantially centered about the collimator opening 33 for creating a two-dimensional cross-section of an X-ray beam emitted from the collimator 33. In this embodiment, optical fiber 47a may be configured to emit a substantially narrow beam having a divergence of the expected divergence of the X-ray beam.

Alternatively, it may be possible to use the optical fiber 47a for visualizing a central axis 45a of the X-ray beam in addition to visualizing the two-dimensional area of the X-ray beam. In this case, the optical fiber may be arranged to emit a narrow beam light producing a miniature light spot on a surface of the patient. In one embodiment, a dimension of the light spot is less than 5 $mm^2$, and more preferably a dimension of the light spot is about 1 $mm^2$. A suitable light emitting diode or a laser may be used for generating light emitted from the fiber 47a. In one embodiment, the light emitting diode and the laser are remotely arranged with respect to the X-ray applicator 30. It will be appreciated that an alternative configuration may be used such as for example, having one or more light sources that may be electrically connected to one or more optical fibers.

Figure 4C:
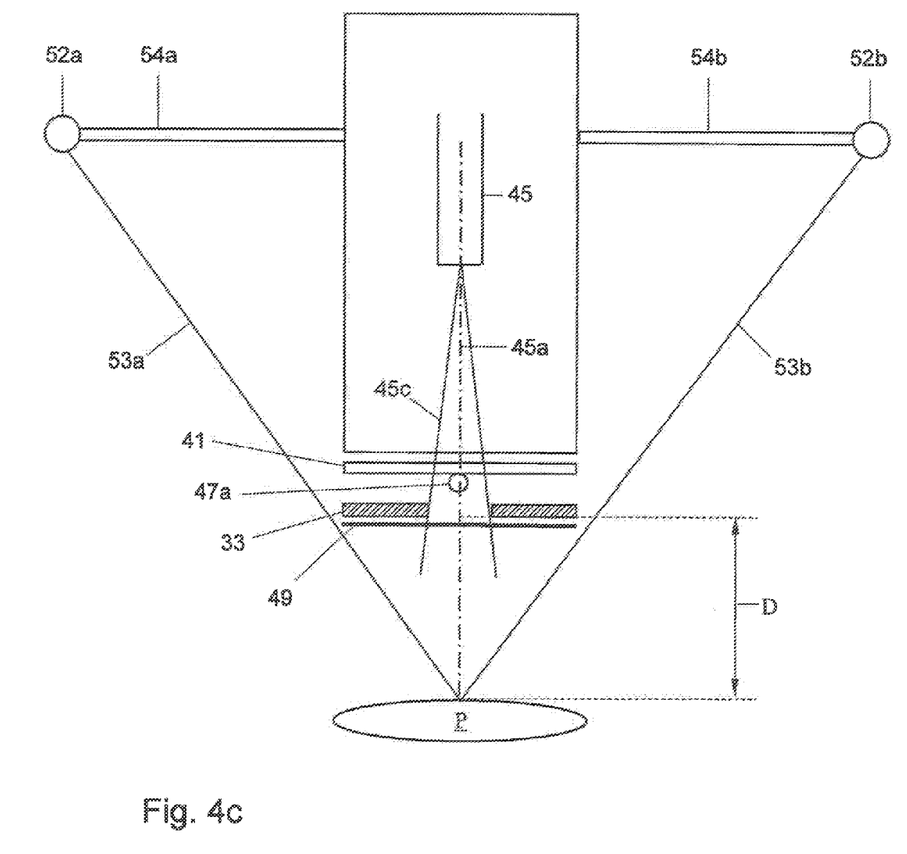
FIG. 4c presents a cross-sectional view of an X-ray applicator of the mobile X-ray unit having an indicator, according to a third embodiment of the present disclosure.

FIG. 4c presents a cross-section of an X-ray applicator 30 of the mobile X-ray unit having an indicator in accordance with a third embodiment of the present disclosure. In this exemplary embodiment, the indicator may be disposed externally of the X-ray applicator 30 and may be one or more light sources 52.

As illustrated in FIG. 4c, the X-ray applicator 30 may include an anode 45 provided with a target for generating an X-ray beam 45c having a longitudinal X-ray axis 45a. The one or more light source 52 may be configured to illuminate the longitudinal axis 45a of the X-ray beam 45c at a pre-determined distance D from the lower surface 49 of the X-ray applicator 30. It will be appreciated that the lower surface 49 may relate to the exit window as discussed with reference to FIG. 1c, or it may relate to the applicator cap, as will be discussed with reference to FIG. 5.

The one or more light sources 52a, 52b may be disposed on support arms 54a, 54b. Light sources 52a, 52b may generate narrow light beams 53a, 53b that may be directed towards the axis 45a and intersect at a pre-determined distance D from the lower surface 49 of the X-ray applicator 30. Preferably, the distance D is selected to be between 0.5 and 2 cm. The support arms 54a, 54b may be arranged so that light beams 53a, 53b do not intersect the X-ray applicator 30.

In use, a user may position the X-ray applicator 30 with respect to the patient P in such a way that the beams 53a, 53b intersect at the surface of the patient. However, should the treatment regime require the use of a dose build-up material, the beams 53a, 53b may cross on a surface of the dose build-up material. In some embodiments, the support arms 54a, 54b may be adjustable to indicate the central axis 45a at different distances from the lower surface 49 of the X-ray applicator 30. In order to calibrate adjustment of the support arms, a transparent calibration phantom may be used, wherein the central axis and depth are marked.

It will be appreciated that although FIGS. 4a-4c disclose separate embodiments of the indicator, a combination of such embodiments is contemplated as well. For example, embodiments directed to indicating the central axis may be combined with embodiments directed to indicating the complete field. In addition, internal and external indicators may be combined.

FIG. 5 presents a partial perspective view of the X-ray applicator provided with an applicator cap. The applicator cap 42 may be manufactured from transparent glass, transparent plastic, or from ceramics as well as from PVDF and PPSU. Applicator cap 42 may also be manufactured from a metal. In the latter case, the applicator cap may be sterilized, otherwise, the applicator cap 42 may be a disposable applicator cap 42. In view 50 of FIG. 4, it is seen that an outer dimension of the X-ray applicator 51 may be larger than the outer dimension of an exit portion covered by the applicator cap 42. Although such embodiment is preferable for minimizing total weight of the X-ray applicator 51, it may be possible that the exit portion has the same dimension as the body of the X-ray applicator 51. In one embodiment, the applicator cap may be 05-2 cm thick when manufactured from a low Z-material.

Figure 6:
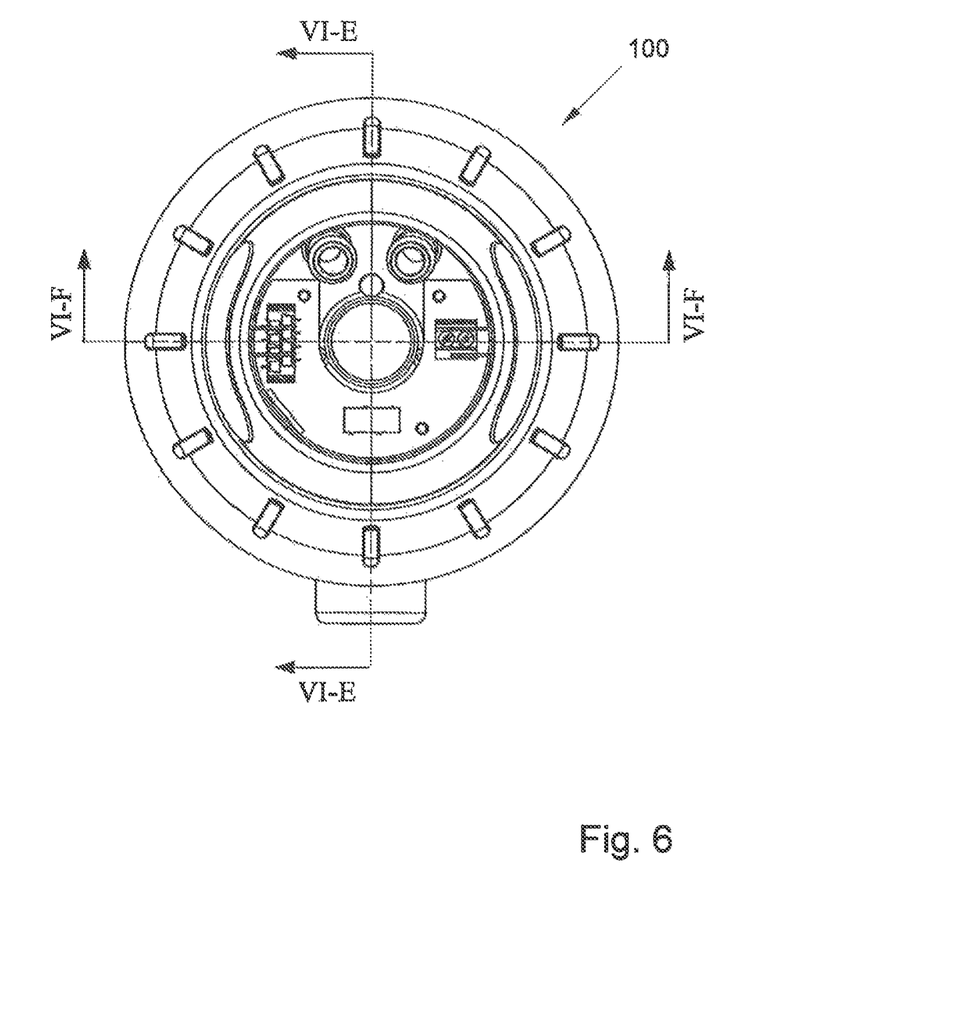
FIG. 6 presents an end view of the X-ray tube, according to embodiments of the present disclosure.

FIGS. 6, 6E-E, and 6F-F, illustrate various views of the X-ray tube. The X-ray tube 100 may have a body 102 enclosing at one end window 104 through which the X-rays pass. See FIG. 8, cross-section E-E. The end window 104 may be made from a thin sheet of Beryllium metal. An applicator cap 106 may be positioned over the end window 104 so as to covering the end window 104 and protect end window 104. Applicator cap 106 may be made from a plastic material. The applicator cap may be manufactured from PVDF (polyvinylidene fluoride) and has a thickness of about 0.4-0.7 mm, and preferably 0.6 mm, across the window portion. Alternatively, the applicator cap 106 may be manufactured from PPSU (polyphenylsulfone) and have a thickness of about 0.3-0.6 mm, and preferably 0.5 mm, across the window portion.

In the tube body 102, a target 108 may be located at a range between 4 and 10 cm from the collimator 130, and preferably between 4 and 5 cm from the collimator 130 (see FIG. 7, cross-section F-F). It will be appreciated that this distance is measured between the outer surface of the target 108 and a midplane of the collimator 130. The target 108 may be made from Tungsten metal to provide the desired X-ray spectrum. The tungsten tip of the target 108 may be mounted on a large anode assembly 110 which also serves to dissipate the heat created from the generation of the X-rays in the target 108. Most of the anode assembly 110 is made from copper. The cathode 112 (see FIG. 7, cross-section F-F) may be located slightly off-axis near the end window 104. Electrons emitted from the cathode are accelerated across the gap by the potential difference between the cathode and anode, in this case set at about 70 kV, to the target 108 where the impact causes the generation of X-rays in a known manner. X-rays emitted from the target 108 pass through a beam hardening filter 122 before passing through a collimator 130 and an exit surface 124 on an applicator cap 106. The collimator 130 may be housed in a suitable collimator receptacle 128.

The anode assembly 110 may be mounted in the body 102 and electrically insulated. One of a number of known techniques and materials may be used to provide the desired level of insulation between the anode assembly 110 and the body 102.

As is well known in the art, the production of X-rays generates a large amount of heat. Accordingly, it may be necessary to cool the X-ray tube 100 in order to maintain it at a safe temperature. Various cooling mechanisms are known and used in the art. In one embodiment, the X-ray tube 100 may be cooled by cooled water forced around the anode region. Cooled water enters the back of the tube by a first conduit 116 and leaves by a second conduit 118 (see FIG. 6, cross-section F-F). The water cooling circuit is a closed loop circuit, with the water leaving the tube assembly 105 to be cooled by a remote cooler (not shown) before returning to the X-ray tube 100. It is contemplated that oil or another liquid may be used as the cooling medium. It is also known that a pressurized gas may be used as an effective coolant in some applications.

As is known in the art, X-rays are generated and emitted in all directions, however the body 102 of the X-ray tube 100 and other internal components will tend to reduce the amount of radiation emitted from the body 102 of the X-ray tube 100 to a minimum, with most of the radiation emitted from the end window 104. The thickness of the shielding provided by the body 102 may be designed so that it provides at least the minimum level of shielding required for safe use by the operator.

A high voltage cable assembly 120 may be connected to the anode assembly 110. The high voltage cable assembly 120 may be connected to flexible cable means (not shown) which in turn may be connected to a high voltage power supply.

A radiation detector 114 may be placed outside the path of the X-ray beam emitted from the target 108 and passing through the end window 104. This detector can be any known form of radiation detector. In one embodiment, the radiation detector may be a hardened semi-conductor connected to an amplifier. The radiation detector 114 may detect when the tube 102 is working and emitting X-ray energy. Output from the detector 114 may connected to a control unit, and the output signals from the detector 114 may be used to provide an optical indication to a user of whether the tube is operating or not. By this means an X-ray detector 114 may be provided which may be used to detect if the X-ray tube is on or off.

With further calibration of the radiation detector 114, it may be possible to determine and calculate the X-ray dose administered to the patient during the treatment. In this manner, it may be possible to have a real time dosimetry measurement system, in which the precise amount of radiation dose administered can be determined. Once the dose rate is known, a treatment plan can be modified during treatment. This may be advantageous because it may enable a very accurate and carefully controlled dose of X-rays to be administered.

In order to enable the X-ray tube 100 to be placed accurately over a tumour, a tumour illumination device may be is used. The tumour illumination device may include a plurality of lights 126 placed around the circumference of the X-ray tube 100 near the end window 104. When in use, the lights shine onto the skin of the patient. Since the lights 126 are positioned around the circumference of the tube body 102, at a short distance from the end of the X-ray tube 100, they create a circle of light with a sharp cut off of the inner part of the circle. In this way, the position of the lights on the tube body 102 may create a shadow. This shadow circle may be used to indicate the region which will be subject to irradiation when the X-ray tube 100 is turned on. It should be appreciated the area within the circle may not be completely dark; the ambient light may be able to enter the shadow region.

In some embodiments, the lights 126 are white LEDs which can be bright enough to clearly illuminate the target region but do not generate large amounts of heat and have very long lives. The lack of heat generation is important because the lights will be in close proximity to the skin of the patient, and so it is important to minimise the risk of burning or other damage to the skin. Other colours of LEDs may be used.

Alternatively, other light sources could be used, such as known filament lamps or even a remote light source connected to the ring by fiber optic cables.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile X-ray unit for irradiating an object, the X-ray unit comprising:
    a base for accommodating a control unit for controlling an X-ray applicator and a power supply for supplying power to the X-ray applicator;
    an arm associated with the base and coupled to the X-ray applicator, wherein the X-ray applicator has an X-ray tube including a body having an exit window at one end thereof for emitting an X-ray beam through the exit window to irradiate the object; and
    a radiation detector provided in the X-ray tube within the body and configured to detect an X-ray beam emitted towards the object.

2. The mobile X-ray unit according to claim 1, wherein the radiation detector is a dosimetry system.

3. The mobile X-ray unit according to claim 1, wherein the radiation detector is positioned outside the path of an X-ray beam passing through the exit window of the X-ray applicator.

4. The mobile X-ray unit according to claim 1, wherein the radiation detector includes a semiconductor detector.

5. The mobile X-ray unit according to claim 1, wherein the radiation detector is configured to verify a position and geometry of an X-ray field.

6. The mobile X-ray unit according to claim 1, wherein the radiation detector is calibrated to determine an absolute dosimetry of an X-ray dose.

7. The mobile X-ray unit according to claim 1, further including at least one light source configured to illuminate at least a portion of the X-ray beam emitted through the exit window of the X-ray applicator.

8. The mobile X-ray unit according to claim 7, wherein the at least one light source includes two light sources concentrically arranged around one of the X-ray tube and the X-ray applicator.

9. The mobile X-ray unit according to claim 8, wherein the X-ray beam has a longitudinal axis, and wherein each light source is arranged to emit a light beam towards the longitudinal axis at a pre-determined distance from a lower surface of the X-ray applicator.

10. The mobile X-ray unit according to claim 7, wherein the light source is disposed inside the X-ray applicator for generating a light beam, wherein a collimator is configured to intercept the light beam and provide a light image of the X-ray field emitted from the exit window.

11. The mobile X-ray unit according to claim 7, further including an optical fiber configured to deliver light from the light source for interception by a collimator.

12. The mobile X-ray unit according to claim 7, further including a plurality of optical fibers distributed in the X-ray applicator in an area above a collimator for illuminating a collimator opening so as to provide a light image of the X-ray field.

13. The mobile X-ray unit according to claim 7, wherein the light source is configured to emit a light beam arranged inside the X-ray applicator to delineate a longitudinal axis of the X-ray beam.

14. The mobile X-ray unit according to claim 1, wherein the radiation detector is configured to generate a signal indicative of the X-ray beam generation.

15. The mobile X-ray unit according claim 1, wherein data obtained by the radiation detector is corrected for a parameter selected from a group consisting of: a temperature of the X-ray tube, an age of the X-ray tube, an angulation of the X-ray tube, and an energy of the X-ray beam.

16. The mobile X-ray unit according to claim 1, wherein the radiation detector is configured to deliver information about radiation dose distribution near a target region.

17. A method for dosimetry control of an X-ray beam emitted from a mobile X-ray unit, the mobile X-ray unit including a base for accommodating a control unit for controlling an X-ray applicator and a power supply for supplying power to the X-ray applicator, an arm associated with the base and coupled to the X-ray applicator, wherein the X-ray applicator has an X-ray tube including a body having an exit window at one end thereof and a radiation detector provided in the X-ray tube within the body, the method comprising:
    controlling the X-ray applicator to generate an X-ray beam; and
    measuring a radiation-related parameter associated with the X-ray beam with the radiation detector provided within the body of the X-ray tube.

18. The method according to claim 17, further including delineating at least a portion of the X-ray beam.

* * * * *